United States Patent [19]

Rowland

[11] Patent Number: 4,561,287

[45] Date of Patent: Dec. 31, 1985

[54] OXYGEN CONCENTRATOR

[75] Inventor: Robert O. Rowland, Hemet, Calif.

[73] Assignee: Hudson Oxygen Therapy Sales Company, Temecula, Calif.

[21] Appl. No.: 634,595

[22] Filed: Jul. 26, 1984

Related U.S. Application Data

[63] Continuation-in-part of Ser. No. 396,705, Jul. 9, 1982, Pat. No. 4,516,424.

[51] Int. Cl.⁴ .............................................. G01N 31/06
[52] U.S. Cl. ............................................ 73/23; 55/21
[58] Field of Search ................. 73/23, 1 G; 55/21, 25, 55/26, 58; 128/205.12, 206.26; 340/632

[56] References Cited

U.S. PATENT DOCUMENTS

| | | | |
|---|---|---|---|
| 3,922,149 | 11/1975 | Ruder et al. | 55/21 |
| 4,197,095 | 4/1980 | White, Jr. et al. | 55/20 |
| 4,247,311 | 1/1981 | Seibert et al. | 55/162 |
| 4,404,005 | 9/1983 | Hamlin et al. | 55/163 |
| 4,428,372 | 1/1984 | Beysel et al. | 55/21 |
| 4,449,990 | 5/1984 | Tedford, Jr. | 55/26 |

FOREIGN PATENT DOCUMENTS 2003742 3/1979 United Kingdom .
2029257 3/1980 United Kingdom .

Primary Examiner—Stephen A. Kreitman
Attorney, Agent, or Firm—Seiler, Quirk & Tratos

[57] ABSTRACT

An oxygen concentrator having molecular sieve beds for selectively adsorbing nitrogen from atmospheric air for increasing the oxygen concentration of a product gas, a reservoir for receiving the product gas, a compressor for charging atmospheric air to the sieve beds and a valve and valve switching means for directing atmospheric air from the compressor to alternate sieve beds includes means for sensing the withdrawal rate of product gas from the reservoir and a microprocessor provided with the minimum time required for charging the respective sieve beds to achieve a product gas having a selected oxygen concentration at the sensed rate of withdrawal and means for switching the valve to charge the beds for the minimum charge time.

22 Claims, 3 Drawing Figures

OXYGEN CONCENTRATOR

REFERENCE TO OTHER APPLICATIONS

This application is a continuation-in-part of my prior co-pending application Ser. No. 396,705, filed July 9, 1982 now U.S. Pat. No. 4,516,424.

BACKGROUND OF THE INVENTION

Oxygen concentrators have become used extensively for supplying oxygen-enriched gas to respiratory patients, particularly those requiring relatively high oxygen concentrations in a breathable gaseous mixture over extended periods of time. Because oxygen concentrators deliver a breathable gas of between about 80–95% oxygen from atmospheric air, thereby eliminating the requirement of bottled gas, oxygen cylinders, and the like, they have found substantial appeal especially in the home care field.

In my aforesaid prior, co-pending application there is described an improved oxygen concentrator which monitors the concentration of the gaseous mixture produced and delivered by the apparatus. In one embodiment a microprocessor monitors the concentration of oxygen in the gaseous mixture produced, and in response adjusts the timing cycle of a valve which directs atmospheric air to the molecular sieve beds from the compressor.

As reliable as oxygen concentrators have become, often power consumption requirements are relatively high. Because of constantly increasing costs of electricity, where such concentrators are required to operate over extended periods of time, as they often are, costs of operation can be substantial, even to the point of otherwise offsetting the convenience of such devices. It is to an improved oxygen concentrator apparatus which automatically adjusts itself for lower power consumption when less than the full operating capacity of the apparatus is required that the present invention is directed.

SUMMARY OF THE INVENTION

In the improved oxygen concentrator assembly of the invention, the pressure of the product gas delivered from the sieve beds to a reservoir tank is monitored so that the withdrawal of product gas is determined. In response to the product gas flow delivered to a user, the timing cycle for pressurizing or charging the molcular sieve beds is varied so that only the minimum amount of atmospheric air is charged to the sieve beds for replenishing the reserovir to meet the gas delivery requirements. When the product gas delivery is less than 4 liters per minute, the power consumption of the compressor is automatically reduced because of the reduced charging times needed to achieve suitable oxygen concentrations in the product gas. To accomplish this function, a gas pressure monitoring transducer in the reservoir tank cooperates with a microprocessor for determining the gas flow from the reservoir, and in response thereto the microprocessor varies the timing sequence of a valve for directing atmospheric air charged to the sieve beds by the compressor.

DETAILED DESCRIPTION OF THE INVENTION

Figure 1:
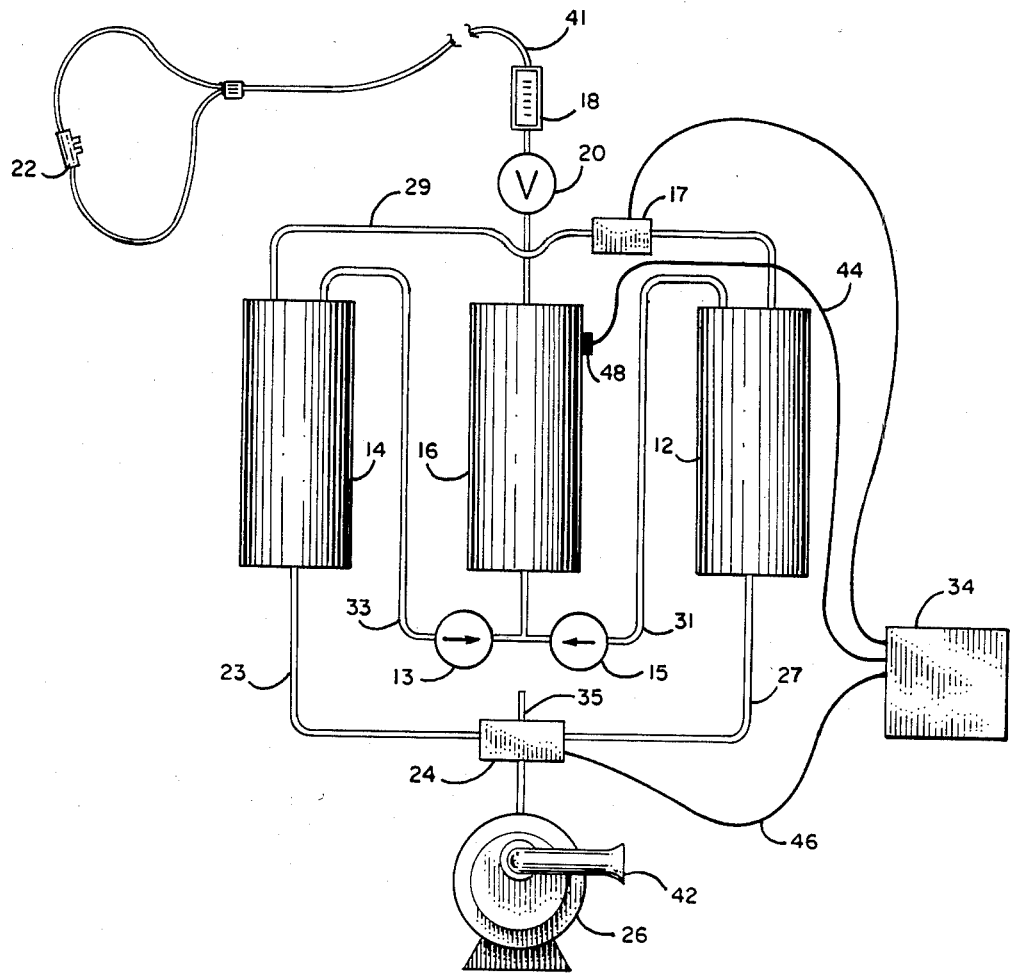
FIG. 1 illustrates schematically the improved oxygen concentrator apparatus of the invention in its basic form.

In FIG. 1, there is illustrated generally the oxygen concentrator of the invention. The apparatus includes a compressor 26 which charges atmospheric air alternately into cannisters 12 and 14 containing molecular sieve material for selectively adsorbing nitrogen from the gas. Between the cannisters is reservoir tank 16 for holding the oxygen-enriched product gas recovered from the sieve beds. Suitable conduits, pipes and valves direct gas between the cannisters and the reservoir.

Generally, in operation, atmospheric air is drawn into compressor 26 via inlet pipe 42 and is forced via pipe 11 to valve 24 where it is alternately directed to sieve bed cannisters 12 and 14. The timing cycle for operating valve 24 is regulated by controller 34 which includes timing means for switching the valve. Atmospheric air is directed under pressure to cannister 12 via conduit 27, and nitrogen is selectively adsorbed from the air as pressure in the cannister is increased. The oxygen enriched product gas from cannister 12 is then directed via conduit 31 through one-way valve 15 into reservoir 16. At a preselected time interval, valve 24 switches the gas flow and directs air to cannister 14 via conduit 23 with the oxygen-enriched product gas passing into reservoir 16 via pipe 33 and one-way valve 13 as previously described. After a sieve bed has gone through a pressurized nitrogen adsorption cycle, pressure is relieved causing release of the adsorbed nitrogen, which is then vented to atmosphere by valve 24 via outlet pipe 35. Thus, the valve simply cycles to pressurize one cannister while the other cannister is being vented, and this cycle continues so long as gaseous product is demanded by use as it is withdrawn from reservoir 16.

The apparatus includes a two-way valve 17 which is open temporarily during a purge cycle whereby oxygen-enriched product gas from one cannister is directed to the other via pipe 29 to assist purging residual nitrogen. The operation of valve 17 including its timing sequence is regulated by a second timing function of controller 34. Near the end of the period when product gas is being directed to the reservoir from one cannister and nitrogen is simultaneously vented from the other, valve 17 opens for a short time to allow a final portion of the oxygen enriched product gas to pass into the venting cannister and purge residual nitrogen. Thus, each cannister alternately adsorbs nitrogen from atmospheric air, the oxygen-enriched gas is directed into reservoir 16, pressure is relieved in the cannister to vent adsorbed nitrogen to atmosphere, and residual nitrogen in the cannister is purged by the flow of oxygen-enriched gas from the other cannister. The cannister is then ready for another charge of atmospheric air to again begin the nitrogen adsorption cycle. Oxygen enriched product gas is withdrawn from reservoir 16 via valve 20 through flow meter 18 it is dispensed to a patient via tube 41 and nasal cannula 22, oxygen mask or other delvery means. The general functioning of oxygen concentrators utilizing two adsorbtion cannisters containing molecular sieve material is well known in the art, and described, for example, in U.S. Pat. Nos. 2,944,627, 3,142,547, 3,280,536, and 3,898,047. Specific portions of these patents for further explaining the operation of oxygen concentrators is incorporated herein by reference.

An improved feature of the invention is in determining product gas withdrawn from reservoir 16 and in response to the withdrawal rate, changing the timing cycle for pressurizing the sieve beds so that minimal charge time is used to still achieve a suitable gas product oxygen concentration at that withdrawal rate. Since the power consumption of the compressor is a direct function of the time and pressure required to charge the sieve beds, by reducing the charging time for pressurizing the beds less power is consumed for operating the compressor. The rate at which product gas is withdrawn from the product reservoir may be monitored by any suitable means such as directly or indirectly monitoring flow control valve settings, measuring pressure differentials across flow control orifices, flow turbine means, and the like, known in the art. In the preferred embodiment of this invention, product gas flow is measured by monitoring the changing pressure in the reservoir utilizing a pressure transducer 48 electrically connected via cable or wire 44 to controller 34. The controller is provided with a microprocessor for determining the flow rate of product gas from reservoir 16 from changes in the pressure sensings. The controller causes pressure samples of the gas in reservoir 16 to be taken at preselected intervals, for example, between about one-half and about five seconds, although any other selected time intervals may be chosen. From these pressure readings, a microprocessor function of controller 34 determines the flow rate of product gas from the reservoir.

The microprocessor function of controller 34 is also provided with information giving the minimum times required for charging the molecular sieve beds with atmospheric air at different flow rates to achieve suitable product gas oxygen concentrations. For example, presently suitable concentrations are about 92-96% at 1-2 liters, 90-92% at 3 liters and 86-90% at 4 liters/minute. To achieve such suitable oxygen concentrations at the 4 liter flow rate requires greater power consumption to operate the compressor as compared to flow rates below 4 liters/minute since the sieve beds must be charged to a relatively high pressure requiring longer compressor charging time and energy. However, because the sieve beds function more effectively at lower flows, less charging time to yield the aforesaid suitable oxygen concentrations are required at the lower flow rates. Presently available oxygen concentrators charge the sieve beds for the same time to the same pressures regardless of product flow rates. According to the present invention, by reducing the required sieve bed charge time and pressure at reduced flow rates take full advantage of sieve bed efficiencies to reduce power consumption without sacrificing suitable oxygen concentrations. Over long periods of concentrator use at product gas withdrawal flows below 4 liters/minute, the apparatus of the invention will result in substantial savings in operating costs. The minimum charging times to achieve such concentrations at the different flow rates are predetermined and that information is provided in memory circuits of the microprocessor of controller 34. The controller is also provided with switching means for switching valve 24 in response to changes in the timing cycle as determined by the flow rate of product gas from reservoir 16. Thus, as the microprocessor of controller 34 determines the flow rate in response to the pressure samplings taken from reservoir 16, the desired timing cycle for minimum charging of the two reservoirs is determined and valve 24 is switched accordingly. The valve is connected to controller 34 via cable 46 for switching the valve according to signals from the controller.

Figure 2:
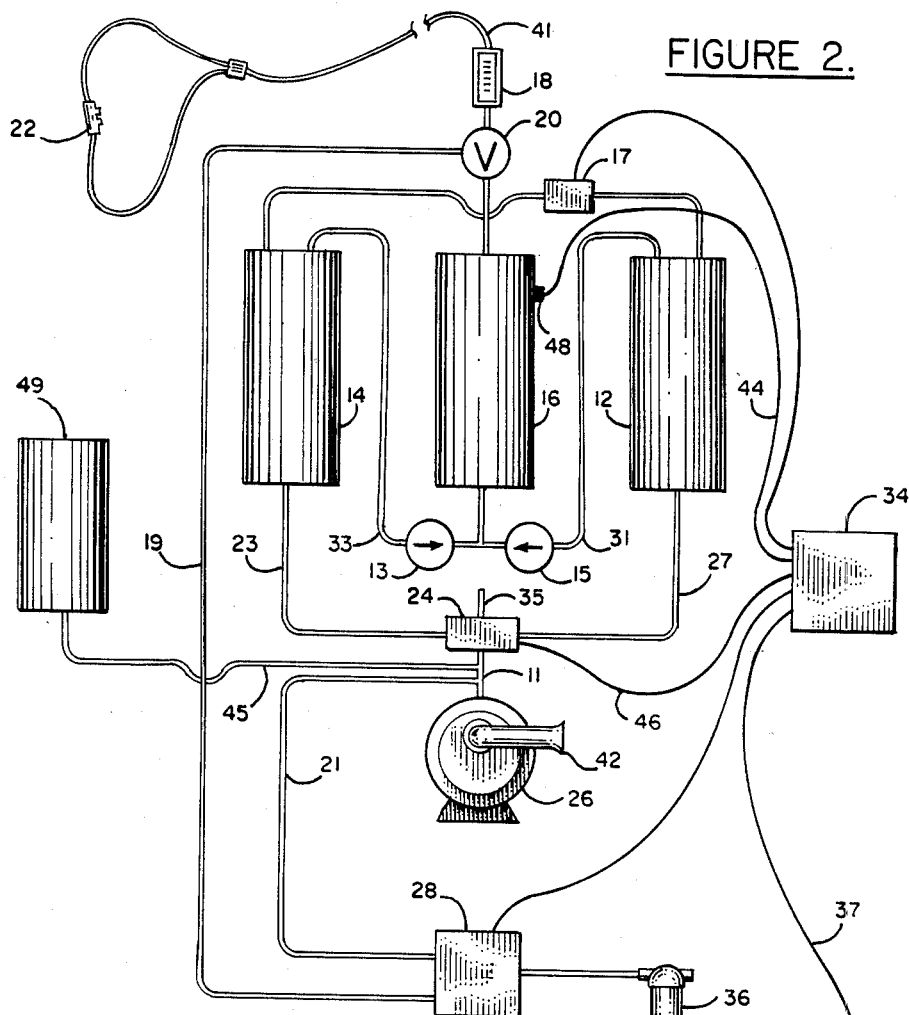
FIG. 2 illustrates an expanded embodiment of the apparatus incorporating a surge tank.

FIG. 2 illustrates a referred embodiment of the oxygen concentrator apparatus, incorporating in addition to the previously described components, a surge tank 49 connected to compressor outlet pipe 11 by conduit 45. The purpose of the surge tank is to receive atmospheric air charged by compressor 26 during the time when niether of the seive bed cannisters 12 and 14 are being pressurized. In this embodiment valve 24 switches from a first position in which cannister 12 is pressurized and cannister 14 is vented and purged, a second position when cannister 14 is pressurized and cannister 12 is vented and purged, and a dead time or intermediate position in which the compressor directs atmospheric air to surge tank 49 when neither cannister is pressurized. This valve functioning and the provision of the surge tank will prevent the compressor from working against a dead-head time during which the valve is closed and passing between the first and second positions. Thus, when the valve is in the intermediate position as it switches between the first and second positions the compressor will charge the surge tank via pipe 45 which is open to pipe 11. Moeover, because the surge tank is pressurized, when the valve is in either the first or second position, pressurized air will pass from the surge tank through the open valve to assist in pressurizing the sieve beds.

In this embodiment, the controller also functions as previously described to regulate the length of time the valve remains in the first and second positions as well as the intermediate position switching time (deadtime) between the first amd second positions for charging the purge tank. Thus, the controller provides the minimum charging times for sieve bed cannisters 12 and 14 to produce the necessary amount of product gas for replenishing reservoir 16 in response to withdrawal of the product gas by a user. At greater product withdrawal rates, more dead time is given when switching from first and second valve positions thereby concomitantly providing for longer charge time for the surge tank. Thus, surge tank charge time is also proportional to the flow rates of product gas from the reservoir.

Figure 3:
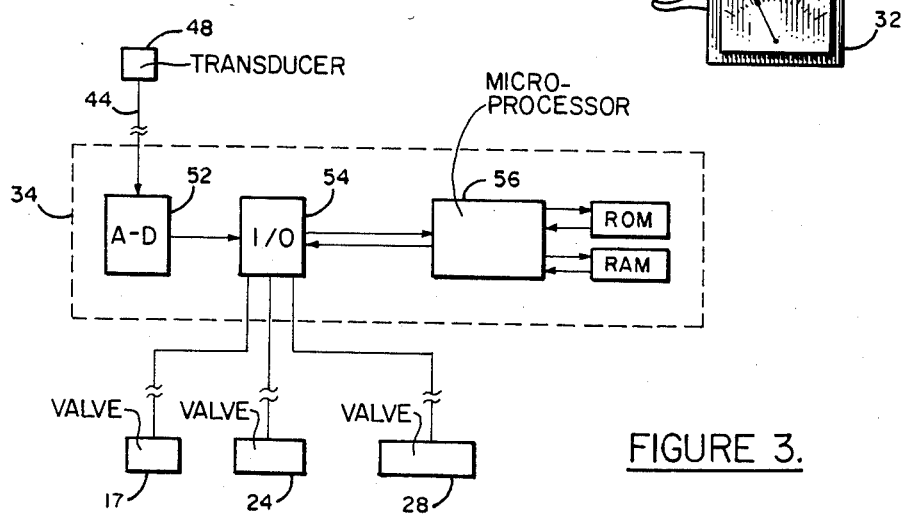
FIG. 3 schematically illustrates the controller circuit of the apparatus.

In FIG. 3 the general design and function of controller 34 is shown schematically. A ROM memory circuit in microprocessor 56 is provided with the minimum charging time requirements for the different product gas flow rates, also taking into consideration the additional charge of atmospheric air available to the sieve beds from a surge tank previously described. Regardless of which apparatus configuration shown is used, pressure sensings from pressure transducer 48 in the reservoir are directed to data acquisition module 52 which provides an A-D function. As previously noted, the controller samples the pressure readings from transducer 48 at preselcted intervals and microprocessor 56 determines the flow rate from the reservoir by comparing the pressure sensings. These pressure sensings are temporarily stored in the RAM memory circuit, usually until the next sensings are taken. The RAM may also temporarily store flow rates determined by the microprocessor. The microprocessor then determines if the time sequence for charging the sieve beds at minimum pressure required to yield suitable oxygen concentrations at the sensed flow rate is correct. If a product gas flow rate change has occurred, the controller selects a different suitable valve timing sequence. The microprocessor signals relays through input/output module 54 to operate valves 24 and 17 in a correct timing sequence. In such an operation when gas product is withdrawn from reservoir 16 at flow rates of less than 4 liters per minute, energy or power requirements for operating compressor 26 are reduced due to the shorter times for charging atmospheric air into sieve bed cannisters 12 and 14. Shorter charging times for pressurizing atmospheric air into the respective sieve bed cannisters to achieve suitable oxygen concentrations in the product gas at flow rates less than 4 liters, reduces energy requirements resulting in substantial cost savings to operate the apparatus. The input/output and data acquisition modules may be components of the controller microprocessor assembly or may be independent components. However, controller 34 shown in the drawings is intended to incorporate any components necessary to achieve the function and operate the apparatus according to the maner described herein.

By way of example, an oxygen concentrator of the type shown in FIG. 2, incororating a compressor rate at ½ hp was operated under the following conditions according to the invention to achieve product gas having the given oxygen concentrations. The sieve bed pressure given is the pressure of each sieve bed during each charge sequence. The dead time is the time the valve was in an intermediate position for charging the surge tank.

| Flow, liters/min. | $O_2$ Con. % | Sieve beds, psi | Surge tank, psi | Dead Time Sec. | Power use watts |
|---|---|---|---|---|---|
| 4 | 90 | 23 | 31 | 1.2 | 420 |
| 3 | 93 | 20 | 26 | 0.4 | 380 |
| 2 | 96 | 16 | 18 | 0.2 | 340 |
| 1 | 96 | 14 | 14 | 0 | 320 |

FIG. 2 also illustrates a further embodiment of the invention incorporating improved gas sampling features set forth in my aforesaid prior co-pending application and incorporated herein. In this embodiment, the apparatus may be provided with components for monitoring the oxygen-enriched gas. In the embodiment shown product gas is directed via pipe 19 through sampling valve 28 which also includes a port for introduction of atmospheric air via pipe 21. The sampling valve, which may be a solenoid valve, will alternately and periodically open and close inlets for pipes 19 and 21 so that oxygen-enriched gas is sampled for a relatively short period of time, and thereafter atmospheric air is sampled. The sampling apparatus shown also includes sensor 36 and monitor 32. In one position valve 28 directs oxygen enriched product gas via pipe 19 to sensor 36. The concentration of the oxygen in the product gas mixture may be observed on the monitor if it includes a meter as shown. The monitor may also be provided with an alarm function whereby a visible and/or audible alarm may be set off when the oxygen concentration is below a preselected minimum or desired value. Controller 34 may also be provided with a timer circuit for operating valve 28 to alternately supply product gas and atmospheric air to the sensor. When valve 28 is switched so that atmospheric air is directed to sensor 36 monitor 32 will calibrate itself to 20.9% oxygen. The time circuit for such a sensor fufnction may provide for product gas sampling for relatively short time periods at selected intervals. Such a feature is particularly advantageous for increasing the life of a galvanic or polorographic sensor such as described in U.S. Pat. No. 4,367,133 or similar electrochemical sensor. Other types of sensors may be used such as sonic or ultrasonic sensors for determining oxygen concentrations in gaseous mixtures. Examples of such devices are shown in U.S. Pat. Nos. 4,280,183, and 2,963,899. Such a sensing device may be used for sensor 36 shown.

In still another embodiment, the controller may be programmed to change the sieve bed charge times to maintain desirable oxygen concentrations in the product gas to compensate for environmental changes such as atmospheric pressure, humidity, temperature, as well as system leaks or sieve bed deterioration and the like. In such an embodiment, controller 34 is connected to monitor 32 via cable 37 so that gas product oxygen concentration sensings are fed to the microcprocessor. A RAM memory circuit will hold the previously sensed oxygen concentration and the microprocessor will determine if the concentrations are changing. Should oxygen concentrations in the product gas begin to drop off, the controller will sense the condition and adjust the charging times for the respective molecular sieve beds and at the delivery rates of the gas product from reservoir 16 by switching valve 24. For this purpose, the microprocessor may compare the sensed concentration with a minimum selected concentration for different flow rates which information is stored in a ROM memory circuit. Should the detected oxygen concentration in product gas be below the minimum acceptable concentration at a given flow rate, the controller will continue to increase the sieve bed charge time until an acceptable concentration is reached. The controller may also be provided with function for limiting the maximum sieve bed charge time, so that, for example, should a gross leak occur in the system, whereby suitable minimum concentration cannot be achieved within a selected time period, the controller will operate an alarm on the monitor.

Preferably, the controller will also include means for terminating operation of the apparatus if suitable product gas oxygen concentrations are not achieved within a preselected period of time. Most suitable components for such a controller function and known to those skilled in the art include suitable logic circuitry or microprocessor cooperating with memory devices, or a microcomputer, and means connected to the controller for operating valve 24 as well as valve 17 to vary the purge times between the cannisters for achieving the desired concentration. Such functioning as is described generally in my aforesaid prior co-pending application is incorporated herein by reference for that purpose.

I claim:

1. In an oxygen concentrator comprising a plurality of molecular sieve beds for alternately receiving atmospheric air and for selectively adsorbing nitrogen therefrom to increase the oxygen concentration of a product gas recovered therefrom, a reservoir for receiving said product gas from said sieve beds, a compressor and a valve cooperating therewith for charging said sieve beds with atmospheric air, valve switching means for alternately charging said sieve beds, and means for withdrawing said product gas from said reservoir, the improvement comprising:

timing means for switching said valve according to a timing cycle, means for sensing the rate of withdrawal of product gas from said reservoir, and a microprocessor having memory means provided with the minimum time required for charging said sieve beds to produce product gas of a selected oxygen concentration at the sensed rate of product gas withdrawal from said reservoir, and means for adjusting the timing cycle for switching said valve to charge said sieve beds for said minimum time.

2. The oxygen concentrator of claim 1 wherein said means for sensing the withdrawal rate of product gas comprises pressure sensing means for sensing gas pressure in said reservoir.

3. The oxygen concentrator of claim 2 wherein said pressure sensing means comprises a transducer in said reservoir.

4. The oxygen concentrator of claim 2 wherein said microprocessor includes means for determining rate of flow of product gas from said reservoir in response to pressure sensings therein.

5. The oxygen concentrator of claim 1 including a surge tank communicating with said compressor for receiving atmospheric air therefrom between the time of alternately charging said sieve beds.

6. The oxygen concentrator of claim 1 including an oxygen sensor for sensing the oxygen concentration of said product gas withdrawn from said reservoir, said microprocessor including memory means provided with minimum selected product gas oxygen concentrations at different product gas withdrawal rates, respectively, means for comparing the sensed product gas oxygen concentration with the minimum selected concentration at the sensed withdrawal rate, and means for adjusting the timing cycle for switching said valve to increase the charging time of said sieve beds to produce a product gas having at least said minimum selected oxygen concentration at the sensed withdrawal rate.

7. The oxygen concentrator of claim 6 wherein said microprocessor includes said timing means.

8. The oxygen concentrator of claim 6 wherein said means for sensing the withdrawal rate of product gas comprises pressure sensing means for sensing gas pressure in said reservoir.

9. The oxygen concentrator of claim 8 wherein said microprocessor includes means for determining rate of flow of product gas from said reservoir in response to pressure sensings therein.

10. The oxygen concentrator of claim 6 including a surge tank communicating with said compressor for receiving atmospheric air therefrom between the time of alternately charging said sieve beds.

11. The oxygen concentrator of claim 6 including means for terminating operation of the apparatus if the minimum selected product gas oxygen concentration is not achieved within a selected period of time.

12. An oxygen concentrator for producing a gaseous product having an increased oxygen concentration from atmospheric air comprising:
a plurality of molecular sieve beds,
a compressor for charging atmospheric air into said sieve beds,
a reservoir for receiving said gaseous product from said sieve beds,
a surge tank for receiving atmospheric air from said compressor,
a valve for directing atmospheric air from said compressor to said sieve beds and said surge tank and switchable between a plurality of different positions for charging different ones of said sieve beds,
means for withdrawing said gaseous product from said reservoir,
means for sensing the gas pressure in said reservoir,
timing means cooperating with said valve for switching said valve between said different positions according to a timing cycle, and
a microprocessor having means for determining the rate of flow of gaseous product from said reservoir in response to pressure sensings therein, memory means provided with the minimum time required for charging said sieve beds to produce gaseous product having a selected oxygen concentration at the determined flow rate from said reservoir, and means for adjusting the timing cycle for switching said valve to charge said sieve beds for said minimum time.

13. An oxygen concentrator for producing a gaseous product having increased oxygen concentration from atmospheric air comprising:
first and second molecular sieve beds for adsorbing nitrogen from said atmospheric air to produce a product gas having a high oxygen concentration,
a compressor for charging atmospheric air into said sieve beds,
a reservoir for receiving said product gas from said sieve beds,
a surge tank for receiving atmospheric air from said compressor and for charging said sieve beds therewith,
a valve having a first position in which atmospheric air is charged into said first sieve bed from said compressor and said surge tank and simultaneously adsorbed nitrogen is vented from said second sieve bed, a second position in which atmospheric air is charged into said second sieve bed from said compressor and said surge tank and simultaneously adsorbed nitrogen is vented from said first sieve bed, and an intermediate position between said first and second positions in which atmospheric air is charged into said surge tank from said compressor,
means for withdrawing said product gas from said reservoir,
means for sensing the rate of withdrawal of product gas from said reservoir,
switching means for switching said valve between said first and second positions, and
microprocessor means cooperating with the product gas withdrawal sensing means and said switching means having memory means provided with the minimum time required for charging said sieve beds to produce product gas of a selected oxygen concentration at the sensed rate said gas is withdrawn from said reservoir, and for switching said valve to said first and second positions for said minimum charging times.

14. In a process for selectively increasing the oxygen concentration of a gaseous mixture comprising switching a valve between a first position to charge atmospheric air under pressure from a compressor into a molecular sieve bed and selectively adsorbing nitrogen therefrom to produce an oxygen enriched gaseous product and a second position in which desorbed nitrogen is released from said sieve bed, directing said gaseous product from said sieve bed to a reservoir, and withdrawing portions of said product from said reservoir, the improvment comprising:

intermittently sensing the pressure of said gaseous product in said reservoir, comparing the intermittent pressures sensed and determining the flow rate of gaseous product withdrawn from said reservoir, adjusting the timing cycle for switching said valve to charge said sieve bed for a minimum time necessary to produce product gas of a selected oxygen concentration at the determined flow rate, and switching said valve according to said adjusted timing cycle.

15. In a process for selectively increasing the oxygen concentration of a gaseous mixture containing oxygen and nitrogen wherein a compressor alternately charges said gaseous mixture under pressure to a first and a second sieve bed, said sieve beds adsorbing nitrogen from said gaseous mixture to produce an oxygen enriched gaseous product and wherein said sieve beds are alternately charged by directing said gaseous mixture to a switching valve having a first valve position in which said compressor charges said first sieve bed and a second position in which said compressor charges said second sieve bed, and directing said gaseous product from said sieve beds to a reservoir, the improvement comprising,
 (a) providing a timing cycle for switching said valve to said first and second positions,
 (b) periodically sensing the pressure of said gaseous product in said reservoir and calculating therefrom the rate of flow of gaseous product withdrawn from said reservoir,
 (c) determining the minimum time required to charge each of said first and second sieve beds to produce a gaseous product having a selected oxygen concentration at the rate of flow said gaseous product is withdrawn from said reservoir,
 (d) adjusting the timing cycle for switching said valve for charging said sieve beds at said minimum required time, and
 (e) switching said valve between said first and second positions according to the adjusted timing cycle, whereby said compressor alternately charges each of said sieve beds for said minimum required time.

16. The process of claim 15 including providing a surge tank communicating with said compressor, said surge tank being charged with atmospheric air from said compressor when said valve is intermediate said first and second positions, and wherein pressurized gas from said surge tank assists in alternately charging said sieve beds when said valve is in said first and second positions, the improvement comprising
 providing a timing cycle for switching said valve to said first and second positions, and switching said valve according to the adjusted timing cycle.

17. In an oxygen concentrator comprising a plurality of molecular sieve beds for alternately receiving atmospheric air and for selectively adsorbing nitrogen therefrom to increase the oxygen concentration of a product gas recovered therefrom, a reservoir for receiving said product gas from said sieve beds, a compressor and valve cooperating therewith for pressurizing said sieve beds with atmospheric air, valve switching means for alternately charging said sieve beds, and means for withdrawing said product gas from said reservoir, the improvement comprising:
 (a) an oxygen sensor for sensing the oxygen concentration of product gas,
 (b) means for sensing the rate of withdrawal of product gas from said reservoir, and
 (c) a microprocessor having
  (1) memory means provided with the minimum time required for charging said sieve beds to produce product gas of a selected oxygen concentration at the sensed rate of withdrawal from said reservoir,
  (2) memory means provided with minimum selected product gas oxygen concentration limits at different withdrawal rates from said reservoir, respectively,
  (3) means for switching said valve for charging said sieve beds for the minimum time required to produce product gas having said selected oxygen concentration at the sensed rate of withdrawal,
  (4) means for comparing the product gas oxygen concentration sensed by said oxygen sensor with the minimum selected product gas oxygen concentration at the sensed withdrawal rate, and
  (5) means for increasing the time for charging said sieve beds to produce product gas having at least the minimum selected oxygen concentration at the sensed withdrawal rate.

18. The oxygen concentrator of claim 17 including a surge tank communicating with said compressor for receiving atmospheric air therefrom between the time of alternately charging said sieve beds.

19. An oxygen concentrator for producing a gaseous product having increased oxygen concentration from atmospheric air comprising:
 first and second molecular sieve beds for adsorbing nitrogen from said atmospheric air to produce a product gas having a high oxygen concentration,
 a compressor for charging atmospheric air into said sieve beds,
 a reservoir for receiving said product gas from said sieve beds,
 a surge tank for receiving atmospheric air from said compressor and for charging said sieve beds therewith,
 a valve having a first position in which atmospheric air is charged into said first sieve bed from said compressor and said surge tank and simultaneously adsorbed nitorgen is vented form said second sieve bed, a second position in which atmospheric air is charged into said second sieve bed from said compressor and said surge tank and simultaneously adsorbed nitrogen is vented from said first sieve bed, and an intermediate position between said first and second positions in which atmospheric air is charged into said surge tank from said compressor,
 means for withdrawing said product gas from said reservoir,
 means for sensing the rate of withdrawal of product gas from said reservoir,
 an oxygen sensor for sensing the oxygen concentration of said product gas withdrawn from said reservoir,
 switching means for switching said valve between said first and second positions, and
 microprocessor means cooperating with the product gas withdrawal sensing means, the oxygen sensor and the valve switching means having memory means provided with minimum selected product gas oxygen concentration limits at different withdrawal rates from said reservoir, respectively, and memory means provided with the minimum time required for charging each of said sieve beds to produce product gas having the minimum selected oxygen concentration at the sensed withdrawal rate, respectively, means for adjusting the timing cycle for operating said switching means for charging said sieve beds for the minimum time required to produce product gas having said minimum selected oxygen concentration at the sensed withdrawal rate, means for comparing the product gas oxygen concentration sensed by said oxygen sensor with said minimum product gas oxygen concentration limit at the sensed withdrawal rate, and means for further adjusting the timing cycle for switching said valve to increase the charging time of said sieve beds necessary to produce product gas having at least said minimum selected oxygen concentration at the sensed withdrawal rate.

20. In a process for selectively increasing the oxygen concentration of a gaseous mixture comprising switching a valve between a first position to charge atmospheric air under pressure from a compressor into a molecular sieve bed and selectively adsorbing nitrogen therefrom to produce an oxygen enriched product gas and a second position in which desorbed nitrogen is released from said sieve bed, directing said product gas to a reservoir, and withdrawing portions of said product gas from said reservoir, the improvement comprising:
(a) determining the minimum time for charging said sieve bed to produce a minimum selected product gas oxygen concentration at a selected rate of withdrawal,
(b) intermittently sensing the rate of withdrawal of product gas from said reservoir,
(c) adjusting a timing cycle for switching said valve to said first and second positions for charging said sieve bed for said minimum time,
(d) intermittently sensing the oxygen concentration of product gas withdrawn from said reservoir,
(e) comparing the sensed oxygen concentration with said minimum selected product gas oxygen concentration, and
(f) adjusting the timing cycle for switching said valve to increase the charging time when the sensed concentration is less than the minimum selected concentration.

21. In a process for selectively increasing the oxygen concentration of a gaseous mixture containing oxygen and nitrogen wherein a compressor alternately charges said gaseous mixture under pressure to a first and a second sieve bed, said sieve beds adsorbing nitrogen from said gaseous mixture to produce an oxygen enriched product gas and wherein said sieve beds are alternately charged by directing said gaseous mixture to a switching valve having a first valve position in which said compressor charges said first sieve bed and a second position in which said compressor charges said second sieve bed, and directing said product gas from said sieve beds to a reservoir, the improvement comprising,
(a) providing a timing cycle for switching said valve to said first and second positions,
(b) periodically determining the rate of withdrawal of product gas from said reservoir,
(c) determining the minimum time required to charge each of said first and second sieve beds to produce a product gas having a minimum selected oxygen concentration at the rate of flow said product gas is withdrawn from said reservoir,
(d) adjusting the timing cycle for switching the valve for charging said sieve beds for said minimum time,
(e) periodically sensing the oxygen concentration of said product gas and comparing the sensed concentration with the minimum selected oxygen concentration at the sensed rate of flow, and
(f) adjusting the timing cycle for switching said valve to increase the charging time when the sensed concentration is less than the minimum selected concentration.

22. In a process for selectively increasing the oxygen concentration of a gaseous mixture comprising switching a valve between a first position to charge atmospheric air under pressure from a compressor into a molecular sieve bed and selectively adsorbing nitrogen therefrom to produce an oxygen enriched gaseous product and a second position in which desorbed nitrogen is released from said sieve bed, directing said gaseous product from said sieve bed to a reservoir, and withdrawing portions of said product from said reservoir, the improvement comprising:
monitoring the rate gaseous product is withdrawn from said reservoir, adjusting the timing cycle for switching said valve to charge said sieve bed for a minimum time necessary to produce gaseous product of a selected oxygen concentration at the monitored rate of withdrawal and switching said valve according to said adjusted timing cycle.

* * * * *